United States Patent
Shimizu et al.

(10) Patent No.: US 12,406,464 B2
(45) Date of Patent: Sep. 2, 2025

(54) INFORMATION PROCESSING DEVICE, INFORMATION PROCESSING SYSTEM, INFORMATION PROCESSING METHOD, AND COMPUTER PROGRAM

(71) Applicant: TERUMO KABUSHIKI KAISHA, Tokyo (JP)

(72) Inventors: Hijiri Shimizu, Hadano (JP); Koichi Inoue, Odawara (JP); Yujiro Matsushita, Atsugi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 370 days.

(21) Appl. No.: 18/180,951

(22) Filed: Mar. 9, 2023

(65) Prior Publication Data

US 2023/0222760 A1  Jul. 13, 2023

Related U.S. Application Data

(63) Continuation of application No. PCT/JP2021/032887, filed on Sep. 7, 2021.

(30) Foreign Application Priority Data

Sep. 14, 2020  (JP) .................................. 2020-154131

(51) Int. Cl.
*G06V 10/60* (2022.01)
*A61B 8/12* (2006.01)
(Continued)

(52) U.S. Cl.
CPC ................ *G06V 10/60* (2022.01); *A61B 8/12* (2013.01); *G06T 7/0012* (2013.01); *G06V 10/25* (2022.01);
(Continued)

(58) Field of Classification Search
CPC ....... G06T 7/0012; G06V 10/25; G06V 10/60
See application file for complete search history.

(56) References Cited

U.S. PATENT DOCUMENTS

| 6,181,810 B1 | 1/2001 | Zhang et al. |
| 2012/0063661 A1 | 3/2012 | Nishimura |
| (Continued) | | |

FOREIGN PATENT DOCUMENTS

| JP | 2002521168 A | 7/2002 |
| JP | 2009195283 A | 9/2009 |
| (Continued) | | |

OTHER PUBLICATIONS

English Translations of the International Search Report (Form PCT/ISA/210) and the Written Opinion of the International Searching Authority (Form PCT/ISA/237) issued Nov. 22, 2021, by the Japan Patent Office in corresponding International Application No. PCT/JP2021/032887. (7 pages).

(Continued)

*Primary Examiner* — Carolyn A Pehlke
(74) *Attorney, Agent, or Firm* — Buchanan Ingersoll & Rooney PC

(57) ABSTRACT

An information processing device including: a control unit configured to: acquire at least one frame image generated by using line data indicating intensity of a reflection wave with respect to an ultrasound radially transmitted from an ultrasound transducer moving inside a biological tissue, and extract a specific region from the at least one frame image based on a ratio between an average of luminance in a region of interest included in the at least one frame image and a dispersion of luminance in the region of interest.

18 Claims, 12 Drawing Sheets

(51) Int. Cl.
*G06T 7/00* (2017.01)
*G06V 10/25* (2022.01)

(52) U.S. Cl.
CPC ............ *G06T 2207/10132* (2013.01); *G06T 2207/30104* (2013.01); *G06V 2201/03* (2022.01)

(56) References Cited

U.S. PATENT DOCUMENTS

| | | |
|---|---|---|
| 2014/0249423 A1 | 9/2014 | Cai et al. |
| 2014/0350404 A1 | 11/2014 | Rajguru et al. |
| 2017/0309018 A1* | 10/2017 | Shalev .................. G06T 7/0012 |

FOREIGN PATENT DOCUMENTS

| | | |
|---|---|---|
| JP | 2015503363 A | 2/2015 |
| JP | 2016511043 A | 4/2016 |
| WO | 2011013346 A1 | 2/2011 |

OTHER PUBLICATIONS

International Search Report (PCT/ISA/210) with translation and Written Opinion (PCT/ISA/237) mailed on Nov. 22, 2021, by the Japan Patent Office as the International Searching Authority for International Application No. PCT/JP2021/032887. (10 pages).

\* cited by examiner

INFORMATION PROCESSING DEVICE, INFORMATION PROCESSING SYSTEM, INFORMATION PROCESSING METHOD, AND COMPUTER PROGRAM

CROSS-REFERENCES TO RELATED APPLICATIONS

This application is a continuation of International Application PCT/JP2021/032887 filed on Sep. 7, 2021, which claims priority to Japanese Application No. 2020-154131 filed on Sep. 14, 2020, the entire content of both of which is incorporated herein by reference.

TECHNOLOGICAL FIELD

The present disclosure generally relates to an information processing device, an information processing system, an information processing method, and a computer program.

BACKGROUND DISCUSSION

Japanese Patent Application Publication No. 2002-521168 A, Japanese Patent Application Publication No. 2015-503363 A, and Japanese Patent Application Publication No. 2016-511043 A describe a technique related to processing of an intravascular ultrasound (IVUS) image.

The IVUS image is acquired by passing a catheter in which an imaging core that transmits and receives ultrasound is rotatably accommodated at a distal end portion of the catheter and is movable in an axial direction through a blood vessel lumen and analyzing a reflection signal of an ultrasound signal received by the imaging core. However, various blood cells such as red blood cells, white blood cells, lymphocytes, and platelets exist in the blood vessel. Therefore, in the IVUS image, a reflection signal mainly from blood cells becomes noise, and it is difficult to observe a region where blood flows and a region of an observation target such as a blood vessel branch, a guide wire, or a stent in detail separately.

SUMMARY

The present disclosure is able to identify an observation target with relatively higher accuracy from a result of observing a cross section of a biological tissue by ultrasound.

An information processing device according to an aspect of the present disclosure includes a control unit acquiring at least one frame image generated by using line data indicating intensity of a reflection wave with respect to an ultrasound radially transmitted from an ultrasound transducer moving inside a biological tissue, and extracting a specific region from the at least one frame image based on a ratio between an average of luminance in a region of interest included in the at least one frame image and a dispersion of luminance in the region of interest.

As an embodiment, the control unit acquires a plurality of frame images as the at least one frame image, and extracts the specific region based on at least one of feature amounts of the plurality of frame images in a time direction and feature amount in another spatial direction, in addition to a ratio between the average of luminance in the region of interest and the dispersion of luminance in the region of interest.

As an embodiment, the control unit extracts a first region from the plurality of frame images based on a ratio between an average of luminance in a first region of interest included in the plurality of frame images and a dispersion of luminance in the first region of interest, extracts a second region from the plurality of frame images based on the at least one feature amount in a second region of interest included in the plurality of frame images, and determines a region commonly included in the first region and the second region as the specific region.

As an embodiment, in a case where a ratio between an average of luminance in a first region of interest and a dispersion of luminance in a first region of interest for a first attentional pixel included in the plurality of frame images falls below a predetermined first value, the control unit determines that the first attentional pixel is included in the first region.

As an embodiment, the control unit calculates, as a feature amount in the time direction, a correlation of luminance between different frame images in the second region of interest for a second attentional pixel included in the plurality of frame images.

As an embodiment, the control unit determines that the second attentional pixel is included in the second region in a case where the feature amount in the time direction falls below a predetermined second value.

As an embodiment, the control unit determines the specific region as a blood flow region.

As an embodiment, the control unit enhances contrast between a region included in the specific region and a region not included in the specific region in the at least one frame image.

As an embodiment, the control unit suppresses luminance of the region included in the specific region in the at least one frame image.

As an embodiment, the control unit causes a display unit to display the at least one frame image by distinguishing the region included in the specific region from the region not included in the specific region.

As an embodiment, the control unit causes the display unit to display the at least one frame image by making display colors different between the region included in the specific region and the region not included in the specific region.

As an embodiment, the control unit causes the display unit to display the at least one frame image by making transparency of the region included in the specific region higher than transparency of the region not included in the specific region.

As an embodiment, the control unit extracts a plurality of types of the specific regions from the at least one frame image based on which of a plurality of predetermined numerical ranges a ratio between an average of luminance in a first region of interest and a dispersion of luminance in the first region of interest for a first attentional pixel included in the at least one frame image belongs to.

As an embodiment, the control unit extracts a plurality of types of the specific regions from the plurality of frame images based on which of a plurality of predetermined first numerical ranges a ratio between an average of luminance in a first region of interest and a dispersion of luminance in the first region of interest for a first attentional pixel included in the plurality of frame images belongs to, and which of a plurality of predetermined second numerical ranges the at least one feature amount in a second region of interest for a second attentional pixel included in the plurality of frame images belongs to.

An information processing system as one aspect of the present disclosure includes the information processing device; and a probe including the ultrasound transducer.

In an information processing method as one aspect of the present disclosure, a control unit of an information processing device acquires at least one frame image generated by using line data indicating intensity of a reflection wave with respect to an ultrasound radially transmitted from an ultrasound transducer moving inside a biological tissue, and extracts a specific region from the at least one frame image based on a ratio between an average of luminance in a region of interest included in the at least one frame image and a dispersion of luminance in the region of interest.

A non-transitory computer-readable medium storing a computer program as one aspect of the present disclosure causes a computer processor to execute processing of: acquiring at least one frame image generated by using line data indicating intensity of a reflection wave with respect to an ultrasound radially transmitted from an ultrasound transducer moving inside a biological tissue; and extracting a specific region from the at least one frame image based on a ratio between an average of luminance in a region of interest included in the at least one frame image and a dispersion of luminance in the region of interest.

According to an embodiment of the present disclosure, it is possible to identify an observation target with higher accuracy from a result of observing a cross section of a biological tissue by ultrasound.

DETAILED DESCRIPTION

Figure 1:
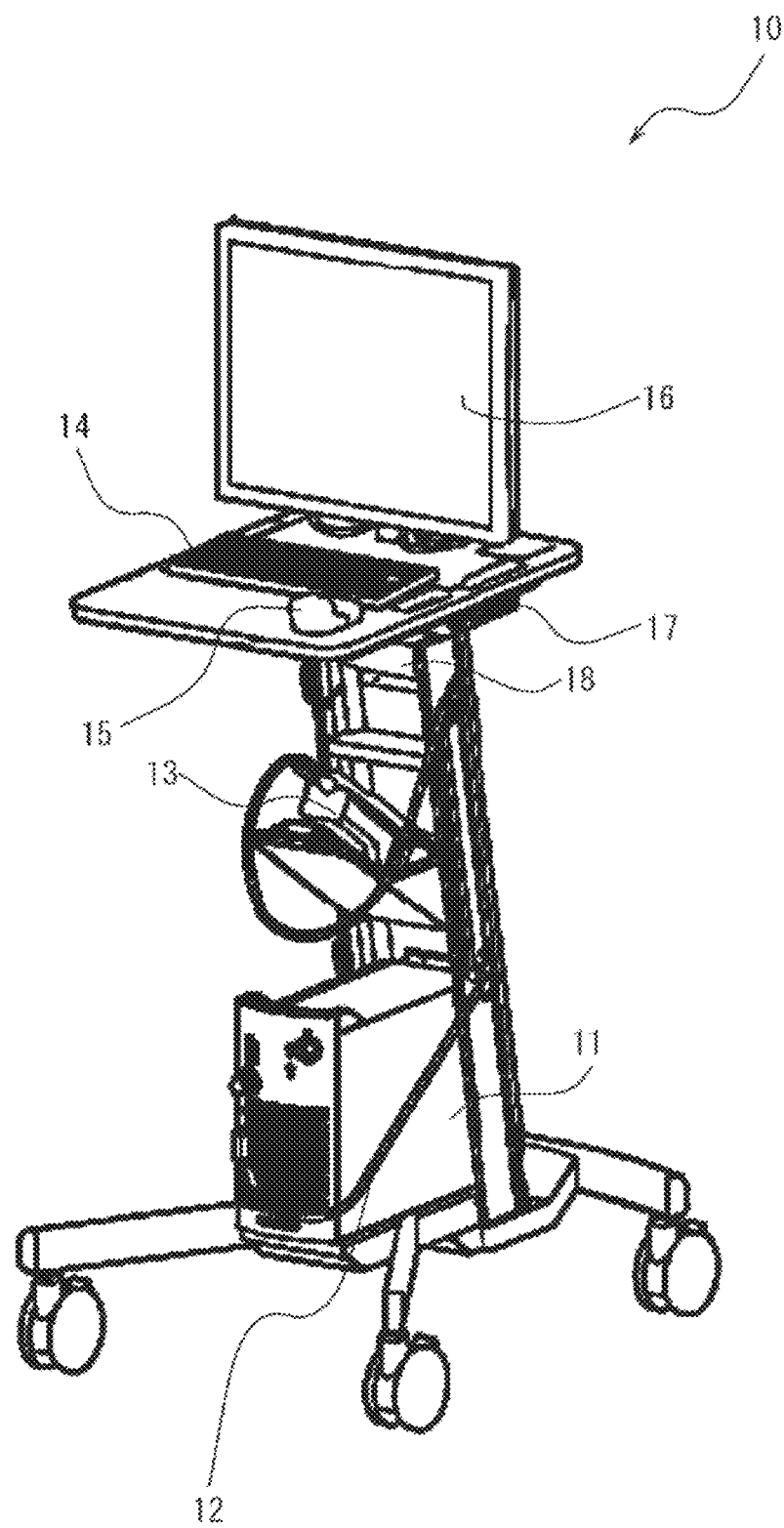
FIG. 1 is a perspective view of a diagnosis support system according to an embodiment of the present disclosure.

Set forth below with reference to the accompanying drawings is a detailed description of embodiments of an information processing device, an information processing system, an information processing method, and a computer program. Note that since embodiments described below are preferred specific examples of the present disclosure, although various technically preferable limitations are given, the scope of the present disclosure is not limited to the embodiments unless otherwise specified in the following descriptions. In the drawings, the same or corresponding portions are denoted by the same reference numerals. In the description of the present embodiment, the description of the same or corresponding parts will be omitted or simplified as appropriate.

System Configuration

A configuration of a diagnosis support system 10 as an information processing system according to the present embodiment will be described with reference to FIG. 1. FIG. 1 is a perspective view of the diagnosis support system 10 according to the present embodiment. The diagnosis support system 10 can include a diagnosis support device 11 as an information processing device, a cable 12, a drive unit 13, a keyboard 14, a pointing device 15, and a display 16.

In the present embodiment, the diagnosis support device 11 is a dedicated computer specialized for image diagnosis, but may be a general-purpose computer such as a personal computer (PC), a workstation (WS), or a tablet terminal.

The cable 12 is used to connect the diagnosis support device 11 and the drive unit 13 to transmit and receive information.

The drive unit 13 is a device that is used by being connected to a probe 20 to be described later and drives the probe 20. The drive unit 13 is also referred to as a motor drive unit (MDU). The probe 20 is applied to IVUS. The probe 20 is also called an IVUS catheter or an image diagnosis catheter. Details of the drive unit 13 and the probe 20 will be described later with reference to FIG. 2.

The keyboard 14, the pointing device 15, and the display 16 are connected to the diagnosis support device 11 via a cable or wirelessly. The display 16 can be, for example, a liquid crystal display (LCD), an organic electro luminescence (EL) display, or a head-mounted display (HMD).

The diagnosis support system 10 optionally further includes a connection terminal 17 and a cart unit 18. The connection terminal 17 is used to connect the diagnosis support device 11 and an external device. The connection terminal 17 can be, for example, a universal serial bus (USB) terminal. The external device can be, for example, a recording medium such as a magnetic disk drive, a magneto-optical disk drive, or an optical disk drive.

The cart unit 18 can be, for example, a cart with a caster for movement. The diagnosis support device 11, the cable 12, and the drive unit 13 can be installed in the cart body of the cart unit 18. The keyboard 14, the pointing device 15, and the display 16 can be installed on the uppermost table of the cart unit 18.

Figure 2:
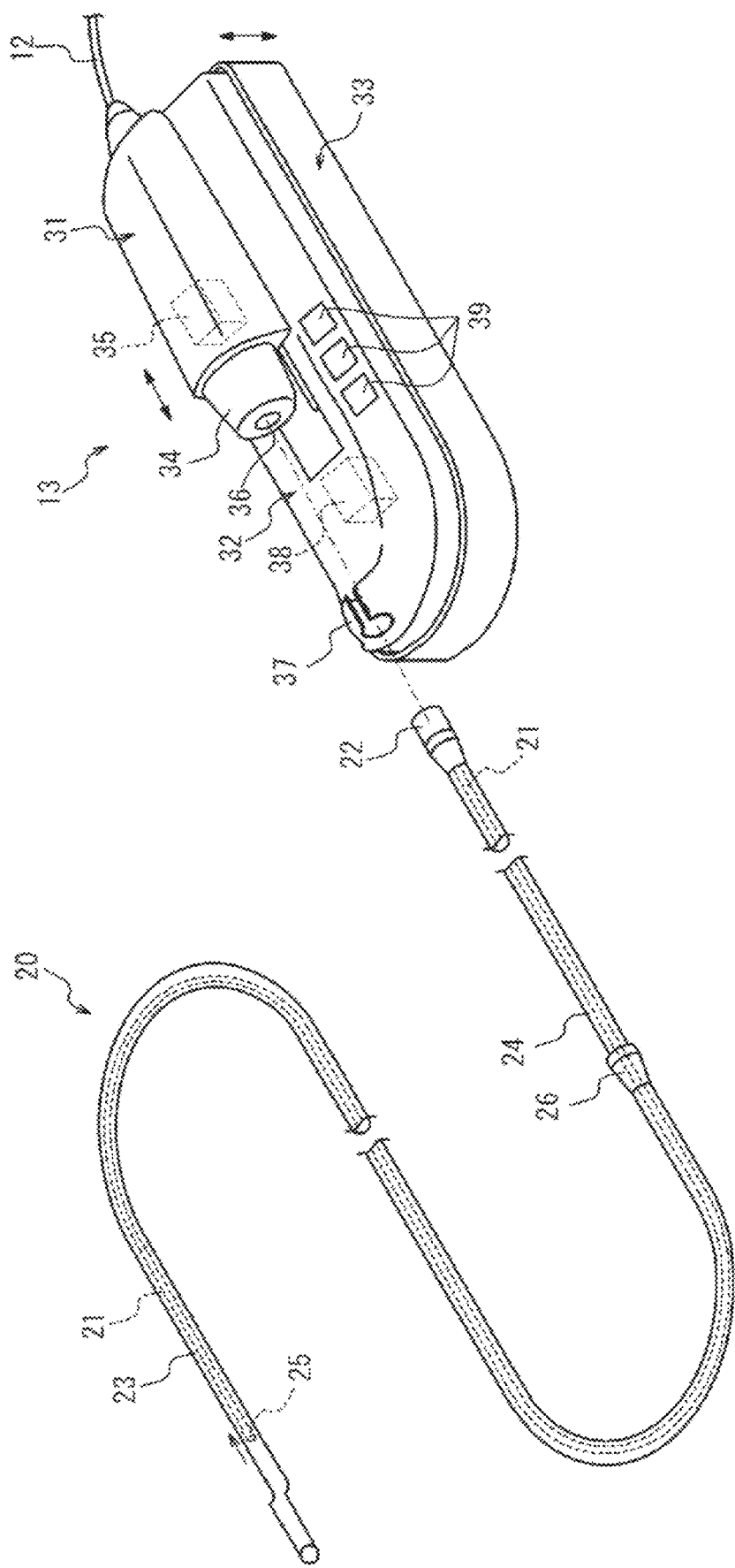
FIG. 2 is a perspective view of a probe and a drive unit according to an embodiment of the present disclosure.

Configurations of the probe 20 and the drive unit 13 according to the present embodiment will be described with reference to FIG. 2. FIG. 2 is a perspective view of the probe 20 and the drive unit 13 according to the present embodiment. The probe 20 can include a drive shaft 21, a hub 22, a sheath 23, an outer tube 24, an ultrasound transducer 25, and a relay connector 26.

The drive shaft 21 passes through the sheath 23 inserted into the body cavity of the living body and the outer tube 24 connected to the proximal end of the sheath 23, and extends to the inside of the hub 22 provided at the proximal end of the probe 20. The drive shaft 21 is rotatably provided in the sheath 23 and the outer tube 24 with an ultrasound transducer 25 that transmits and receives a signal at the distal end. The relay connector 26 connects the sheath 23 and the outer tube 24.

The hub 22, the drive shaft 21, and the ultrasound transducer 25 are connected to each other to integrally moves forward and backward in the axial direction of the probe 20. Therefore, for example, when the hub 22 is pushed toward the distal end side, the drive shaft 21 and the ultrasound transducer 25 move to the distal end side inside the sheath 23. For example, when the hub 22 is pulled toward the proximal end side, the drive shaft 21 and the ultrasound transducer 25 move toward the proximal end side inside the sheath 23 as indicated by arrows in FIG. 2.

The drive unit 13 can include a scanner unit 31, a slide unit 32, and a bottom cover 33. The scanner unit 31 is connected to the diagnosis support device 11 via the cable 12.

The scanner unit 31 can include a probe connection portion 34 connected to the probe 20 and a scanner motor 35 as a drive source for rotating the drive shaft 21. The probe connection portion 34 is detachably connected to the probe 20 via an insertion port 36 of the hub 22 provided at the proximal end of the probe 20. In the hub 22, the proximal end of the drive shaft 21 is rotatably supported, and the rotational force of the scanner motor 35 is transmitted to the drive shaft 21. In addition, signals are transmitted and received between the drive shaft 21 and the diagnosis support device 11 via the cable 12. In the diagnosis support device 11, generation of a tomographic image of a biological lumen and image processing are performed based on a signal transmitted from the drive shaft 21.

The slide unit 32 is mounted with the scanner unit 31 to be movable forward and backward, and is mechanically and electrically connected to the scanner unit 31. The slide unit 32 can include a probe clamp portion 37, a slide motor 38, and a switch group 39.

The probe clamp portion 37 is provided at a position coaxial with the distal end side of the probe connection portion 34, and supports the probe 20 connected to the probe connection portion 34.

The slide motor 38 is a drive source that generates a drive force in the axial direction of the probe 20. The scanner unit 31 moves forward and backward by the drive of the slide motor 38, and the drive shaft 21 moves forward and backward in the axial direction of the probe 20 accordingly. The slide motor 38 can be, for example, a servo motor.

The switch group 39 can include, for example, a forward switch and a pull-back switch that are pressed at the time of the forward and backward operation of the scanner unit 31, and a scan switch that is pressed at the time of the start and end of image depiction. The present disclosure is not limited to the examples described in the disclosure, and various switches are included in the switch group 39 as necessary.

When the forward switch is pressed, the slide motor 38 rotates forward, and the scanner unit 31 moves forward. As a result, the hub 22 connected to the probe connection portion 34 of the scanner unit 31 is pushed out toward the distal end side, and the drive shaft 21 and the ultrasound transducer 25 move to the distal end side inside the sheath 23. On the other hand, when the pull-back switch is pressed, the slide motor 38 reversely rotates, and the scanner unit 31 moves backward. As a result, the hub 22 connected to the probe connection portion 34 is swept to the proximal end side, and the drive shaft 21 and the ultrasound transducer 25 move to the proximal end side inside the sheath 23.

When the scan switch is pressed, image depiction is started, the scanner motor 35 is driven, and the slide motor 38 is driven to move the scanner unit 31 backward. A user such as an operator connects the probe 20 to the scanner unit 31 in advance, and causes the drive shaft 21 to move to the axial proximal end side while rotating around the central axis of the probe 20 at the start of image depiction. When the scan switch is pressed again, the scanner motor 35 and the slide motor 38 are stopped, and image depiction ends.

The bottom cover 33 covers the entire periphery of the bottom surface and the side surface on the bottom surface side of the slide unit 32, and can approach and separate from the bottom surface of the slide unit 32.

Figure 3:
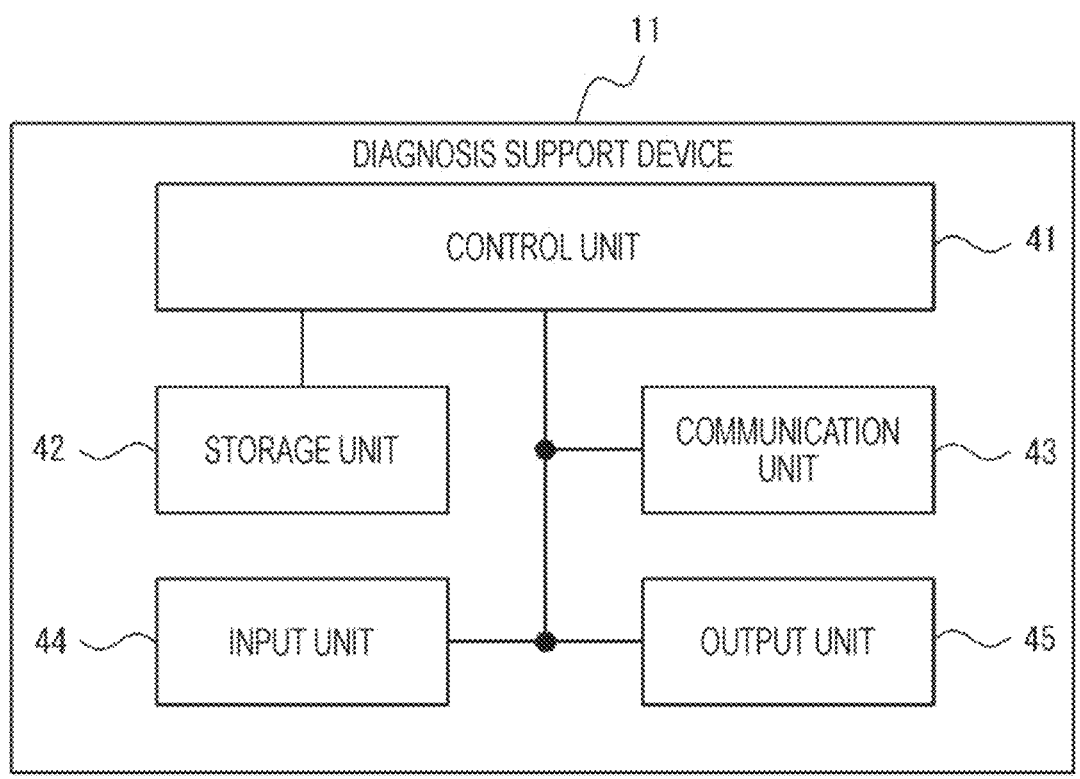
FIG. 3 is a block diagram illustrating a configuration of a diagnosis support device according to an embodiment of the present disclosure.

A configuration of the diagnosis support device 11 according to the present embodiment will be described with reference to FIG. 3. The diagnosis support device 11 can include components such as a control unit 41, a storage unit 42, a communication unit 43, an input unit 44, and an output unit 45.

The control unit 41 can be one or more processors. The processor can be, for example, a general-purpose processor such as a central processing unit (CPU) or a graphics processing unit (GPU), or a dedicated processor specialized for specific processing. The control unit 41 may include one or more dedicated circuits, or one or more processors may be replaced with one or more dedicated circuits in the control unit 41. The dedicated circuit is, for example, a field-programmable gate array (FPGA) or an application specific integrated circuit (ASIC). The control unit 41 executes information processing related to the operation of the diagnosis support device 11 while controlling each unit of the diagnosis support system 10 including the diagnosis support device 11.

The storage unit 42 can be one or more semiconductor memories, one or more magnetic memories, one or more optical memories, or a combination of at least two of these. The semiconductor memory can be, for example, a random access memory (RAM), i.e., writable memory or a read only memory (ROM). The RAM can be, for example, a static random access memory (SRAM) or a dynamic random access memory (DRAM). The ROM can be, for example, an electrically erasable programmable read only memory (EEPROM). The storage unit 42 can function as, for example, a main storage device, an auxiliary storage device, or a cache memory. The storage unit 42 stores information used for the operation of the diagnosis support device 11 and information acquired by the operation of the diagnosis support device 11.

The communication unit 43 is one or more communication interfaces. The communication interface is a wired local area network (LAN) interface, a wireless LAN interface, or an image diagnosis interface that receives and analog to digital (A/D) converts an IVUS signal. The communication unit 43 receives information used for the operation of the diagnosis support device 11 and transmits information acquired by the operation of the diagnosis support device 11. In the present embodiment, the drive unit 13 is connected to the image diagnosis interface included in the communication unit 43.

The input unit 44 is one or more input interfaces. The input interface is, for example, a USB interface or a highdefinition multimedia interface (HDMI®) interface. The input unit 44 receives an operation of inputting information used for the operation of the diagnosis support device 11. In the present embodiment, the keyboard 14 and the pointing device 15 can be connected to the USB interface included in the input unit 44, but the keyboard 14 and the pointing device 15 may be connected to the wireless LAN interface included in the communication unit 43.

The output unit 45 is one or more output interfaces. The output interface can be, for example, a USB interface or an HDMI interface. The output unit 45 outputs information acquired by the operation of the diagnosis support device 11. In the present embodiment, the display 16 is connected to an HDMI interface included in the output unit 45.

The function of the diagnosis support device 11 can be realized by executing a diagnosis support program (computer program) according to the present embodiment by a processor included in the control unit 41. That is, the function of the diagnosis support device 11 is realized by software. The diagnosis support program is a program for causing a computer to execute processing of steps included in the operation of the diagnosis support device 11, causing the computer to realize a function corresponding to the processing of the steps. That is, the diagnosis support program is a program for causing a computer to function as the diagnosis support device 11.

The program can be recorded in a computer-readable recording medium. The computer-readable recording medium is, for example, a magnetic recording device, an optical disk, a magneto-optical recording medium, or a semiconductor memory. The distribution of the program can be performed, for example, by selling, transferring, or renting a portable recording medium such as a digital versatile disc (DVD) or a compact disc read only memory (CD-ROM) in which the program is recorded. The program may be distributed by storing the program in a storage of a server and transferring the program from the server to another computer via a network. The program may be provided as a program product.

For example, the computer temporarily stores a program recorded in a portable recording medium or a program transferred from a server in a main storage device. Then, the computer reads the program stored in the main storage device by the processor, and executes processing according to the read program by the processor. The computer may read the program directly from the portable recording medium and execute processing according to the program. The computer may sequentially execute processing according to the received program each time the program is transferred from the server to the computer. The processing may be executed by a so-called application service provider-type (ASP-type) service that realizes a function only by an execution instruction and result acquisition without transferring the program from the server to the computer. The program includes information that is used for processing by an electronic computer and is equivalent to the program. For example, data that is not a direct command to the computer but has a property that defines processing of the computer corresponds to "information based on a program".

Some or all of the functions of the diagnosis support device 11 may be realized by a dedicated circuit included in the control unit 41. That is, a part or all of the functions of the diagnosis support device 11 may be realized by hardware. In addition, the diagnosis support device 11 may be realized by a single information processing device or may be realized by cooperation of a plurality of information processing devices.

Acquisition of IVUS Image

With reference to FIGS. 4A to 4E, a principle of acquiring an IVUS image will be described. FIG. 4A to 4E are diagrams illustrating an example in which an IVUS image is acquired by the diagnosis support device 11 according to the present embodiment.

As described above, during the imaging of the IVUS image, the drive shaft 21 is pulled back to the proximal end side where the drive unit 13 is present in accordance with the backward movement of the scanner unit 31 while rotating around the central axis of the probe 20. The ultrasound transducer 25 provided at the distal end of the drive shaft 21 also moves to the proximal end side of the probe 20 while rotating around the central axis of the probe 20 in conjunction with the drive shaft 21 while transmitting and receiving an ultrasound signal inside a biological tissue such as a blood vessel.

Figure 4A:
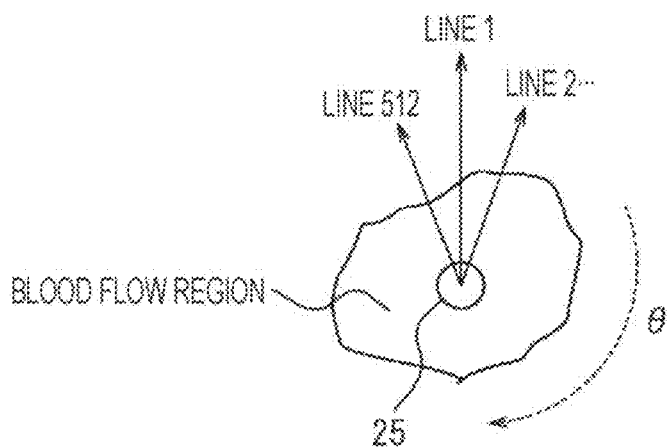
FIG. 4A is a diagram illustrating an example in which an IVUS image is acquired by the diagnosis support device according to an embodiment of the present disclosure.

FIG. 4A schematically illustrates a flat surface passing through the position where the ultrasound transducer 25 is present and orthogonal to the central axis of the probe 20. The ultrasound transducer 25 radially transmits a pulse wave of an ultrasound while rotating at a constant speed around the central axis of the probe 20 in the biological tissue, receives a reflection wave of the pulse wave from each radial direction (i.e., radial directions at different angles, for example, Line 1, Line 2, . . . , Line 512 as shown in FIG. 4A), and generates a reception signal. FIGS. 4A to 4E illustrate an example in which 512 pulse waves are transmitted at equal intervals while the ultrasound transducer 25 rotates 360 degrees, and a reception signal of a reflection wave from each direction is generated. In this manner, in the entire circumference of the ultrasound transducer 25, each direction in which the pulse of the ultrasound wave is transmitted is referred to as a line (scanning line), and data indicating the intensity of the reflection wave of the ultrasound wave in each line is referred to as line data.

Figure 4B:
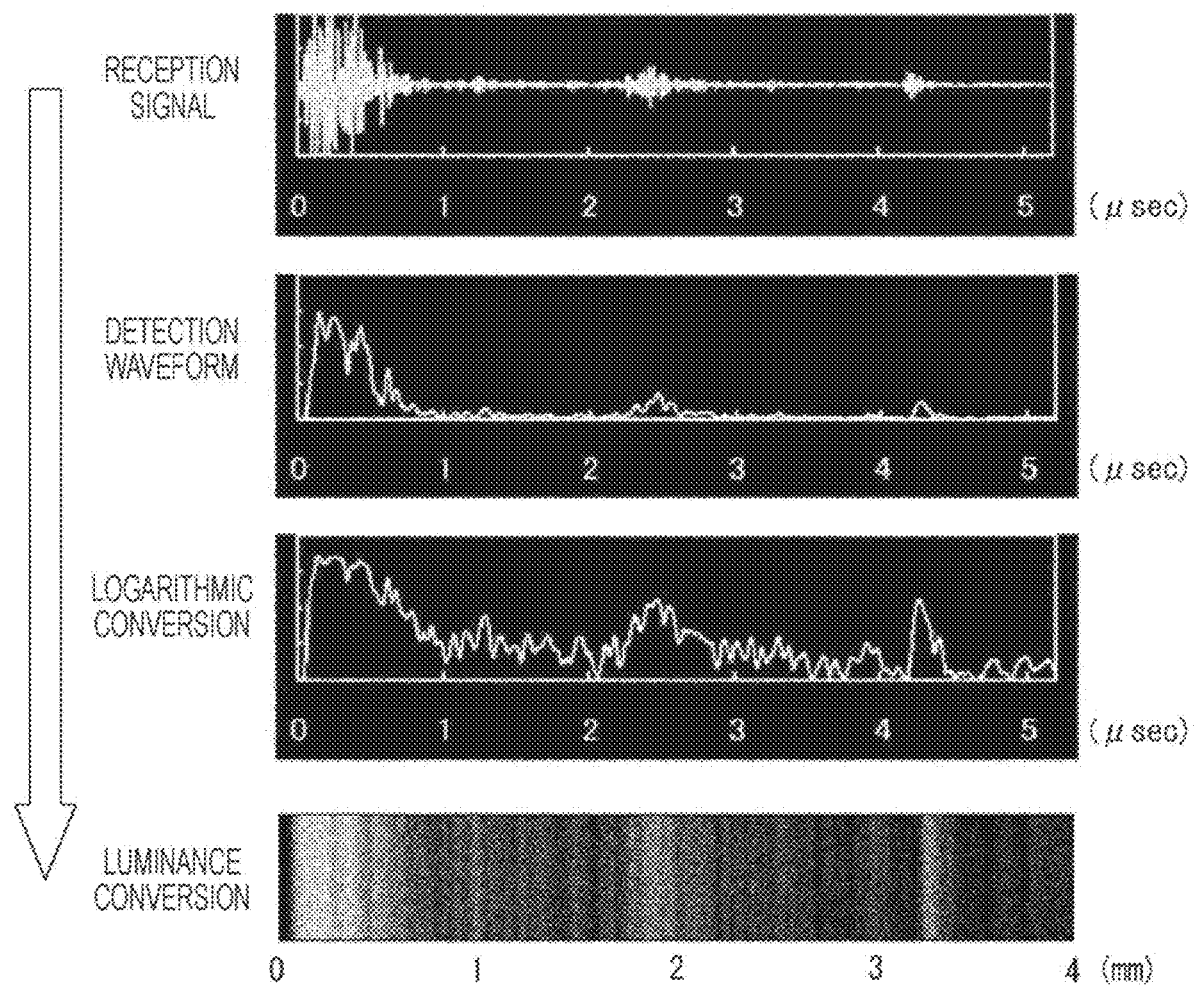
FIG. 4B is a diagram illustrating an example in which an IVUS image is acquired by the diagnosis support device according to an embodiment of the present disclosure.

FIG. 4B illustrates an example in which a luminance image is acquired by performing luminance conversion on a reception signal of a reflection wave in each line. As illustrated in FIG. 4B, the reception signal of each line is converted into a detection waveform indicating an amplitude of the reception signal, and logarithmic conversion is performed. Then, luminance conversion is performed to associate the signal intensity with the luminance in the image. The control unit 41 of the diagnosis support device 11 constructs luminance data for one line by assigning 256 gray scale colors according to the intensity of the reflection signal, for example. The horizontal axis of each diagram in FIG. 4B indicates time, and the vertical axis of the reception signal, the detection waveform, and the logarithmic conversion indicates signal intensity. Since the speed at which the ultrasound is transmitted is constant, the time from the transmission of the ultrasound to the reception of the reflection wave is proportional to the distance between the ultrasound transducer 25 and the object that has reflected the ultrasound. Therefore, the line data obtained by the processing of FIG. 4B is data indicating the intensity of the reflection signal according to the distance from the ultrasound transducer 25 by the luminance of the image.

Figure 4C:
FIG. 4C is a diagram illustrating an example in which an IVUS image is acquired by the diagnosis support device according to an embodiment of the present disclosure.
Figure 4D:
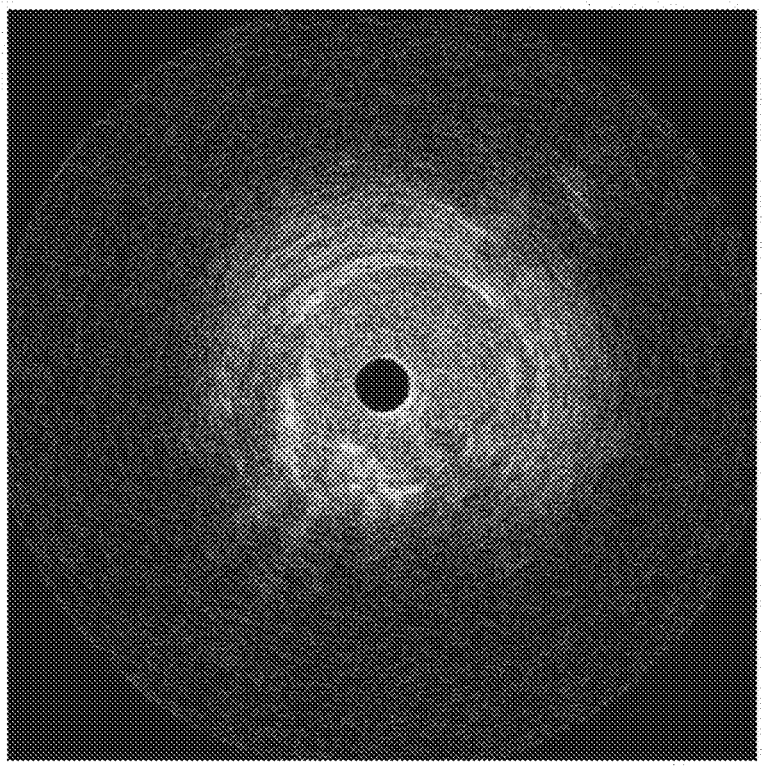
FIG. 4D is a diagram illustrating an example in which an IVUS image is acquired by the diagnosis support device according to an embodiment of the present disclosure.

FIG. 4C illustrates an example in which the line data of the lines 1 to 512 subjected to the luminance conversion are stacked and displayed. By performing the polar coordinate conversion on this image, a cross-sectional image of the biological tissue as illustrated in FIG. 4D is acquired. One cross-sectional image is generated by 512 pieces of line data acquired while the ultrasound transducer 25 rotates 360 degrees about the central axis of the probe 20. Such a one cross-sectional image is referred to as a frame image, and its data is referred to as frame data. The position of each pixel included in the frame image according to the IVUS image is specified by a distance r from the ultrasound transducer 25 and a rotation angle θ of the ultrasound transducer 25 from the reference angle.

Figure 4E:
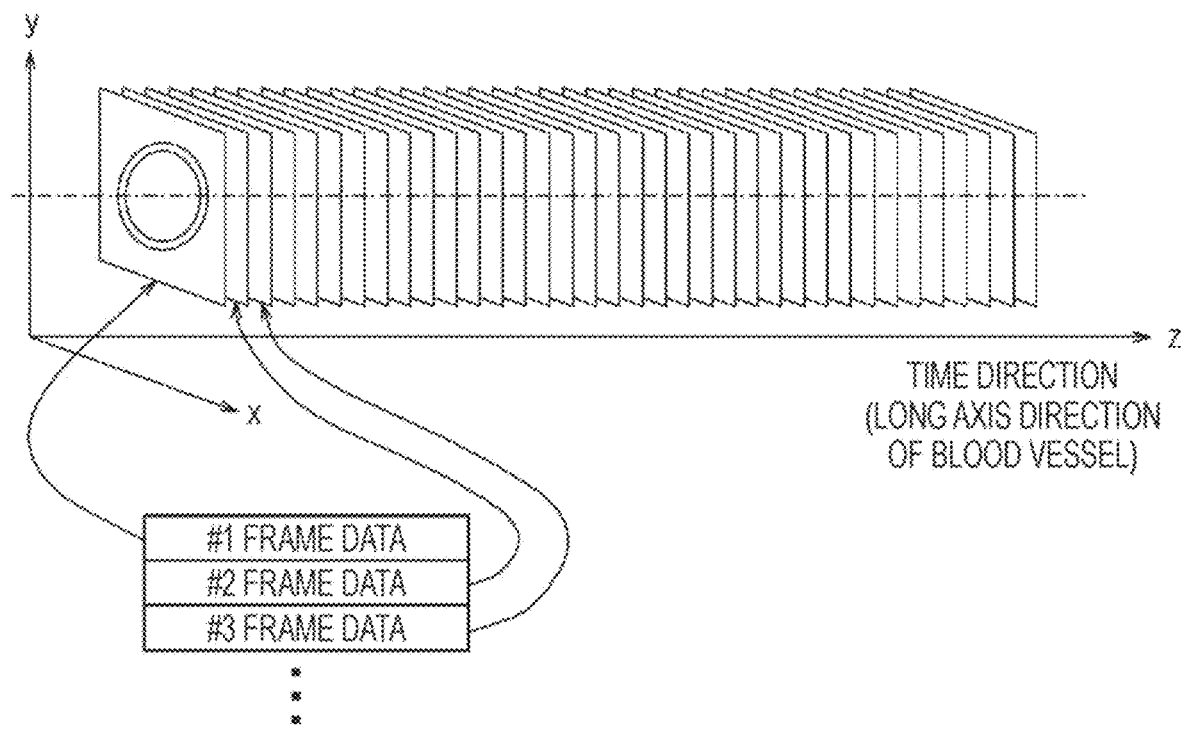
FIG. 4E is a diagram illustrating an example in which an IVUS image is acquired by the diagnosis support device according to an embodiment of the present disclosure.

As described above, the IVUS image is acquired while the ultrasound transducer 25 is pulled back to the proximal end side of the probe 20. Therefore, as illustrated in FIG. 4E, when the ultrasound transducer 25 moves in the blood vessel, the imaging catheter (probe 20) is swept (pulled back) in a longitudinal direction (i.e., long axis direction) of the blood vessel to acquire continuous frame data. Here, since the ultrasound transducer 25 acquires frame data one by one while moving, the longitudinal axis direction of the blood vessel in a plurality of pieces of frame data continuously acquired corresponds to the time direction. Hereinafter, two directions orthogonal to each other in the same frame image are referred to as spatial directions to be distinguished from time directions. In FIG. 4E, the x direction and the y direction correspond to a spatial direction, and the z direction corresponds to a time direction. In FIGS. 4A to 4E, the example in which the number of pieces of line data acquired every time the probe 20 makes one rotation is 512 has been described, but the number of pieces of line data is not limited to 512, and may be, for example, 256 or 1024.

Operation Example

As described above, the IVUS image is acquired as at least one frame image generated using the line data indicating the intensity of the reflection wave with respect to the ultrasound radially transmitted from the ultrasound transducer 25 moving inside the biological tissue. The diagnosis support device 11 according to the present embodiment extracts the specific region from the at least one frame image based on the ratio between the average of the luminance in the region of interest included in the at least one frame image and the dispersion of the luminance in the region of interest. An operation of the diagnosis support system 10 according to the present embodiment will be described with reference to FIGS. 5A and 5B. The operation of the diagnosis support device 11 described with reference to FIGS. 5A and 5B corresponds to the information processing method according to the present embodiment, and the operation of each step is executed based on the control of the control unit 41.

Figure 5A:
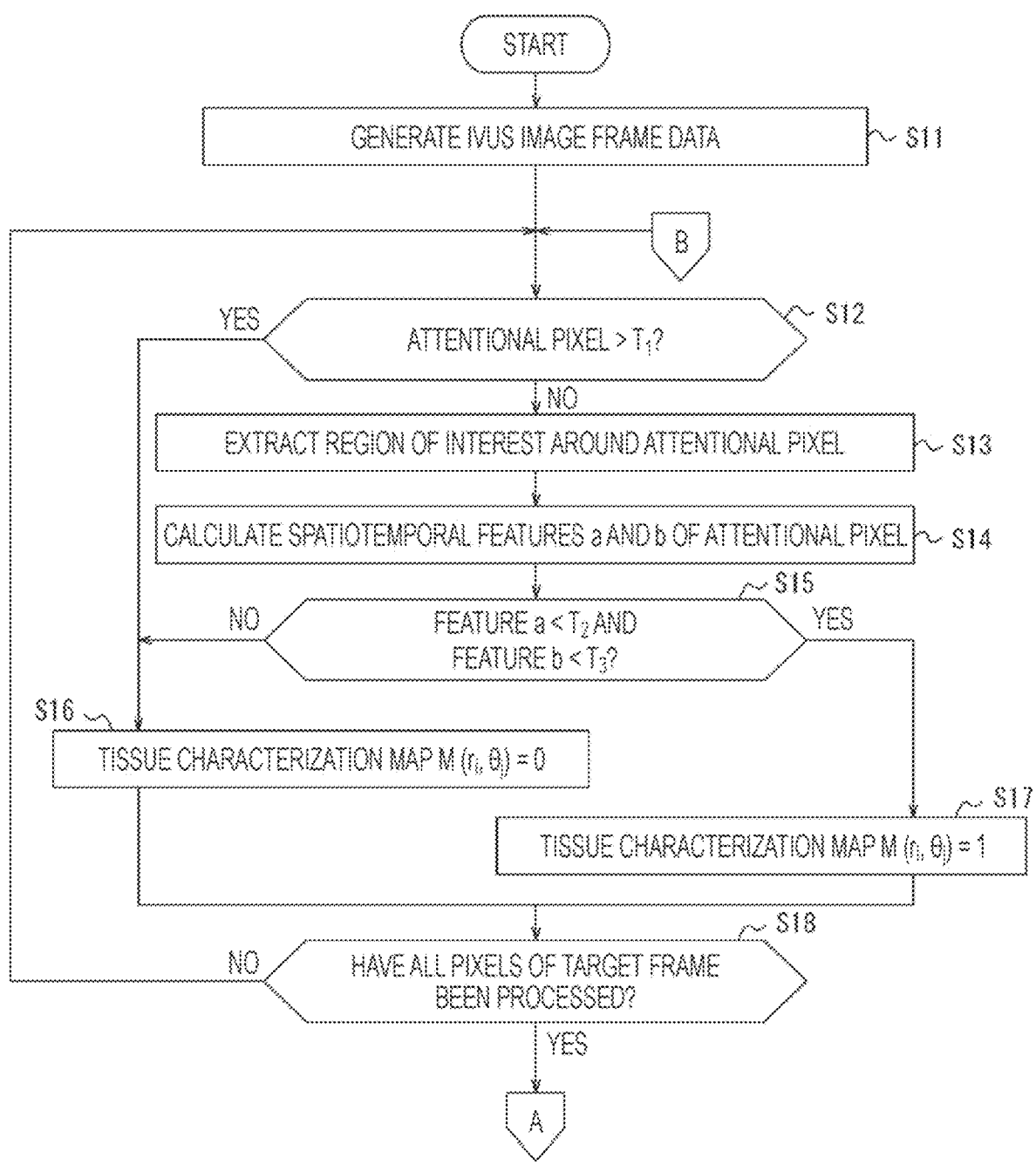
FIG. 5A is a flowchart illustrating an operation of the diagnosis support device according to an embodiment of the present disclosure.
Figure 5B:
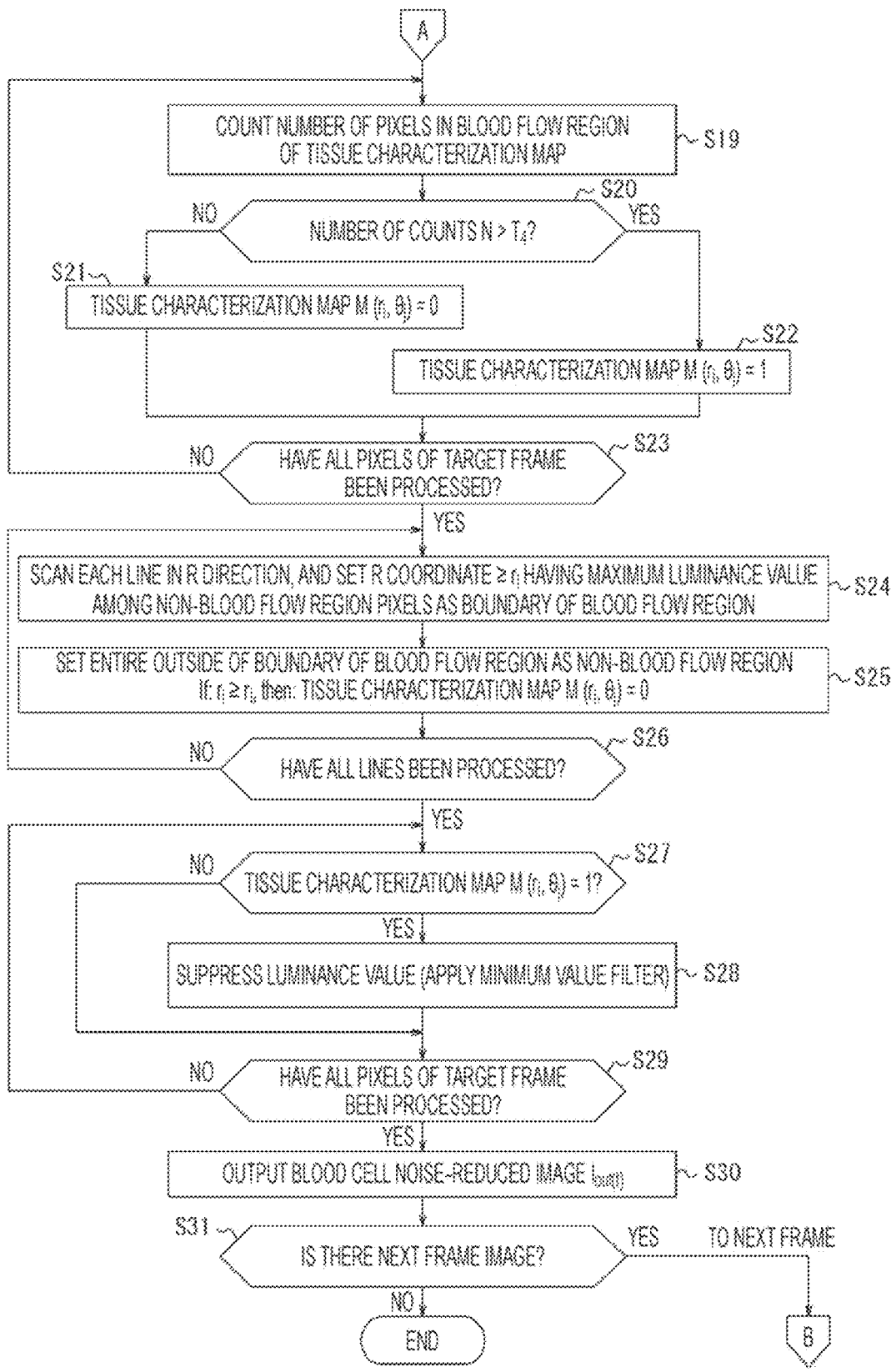
FIG. 5B is a flowchart illustrating an operation of the diagnosis support device according to an embodiment of the present disclosure.

Before the start of the flow of FIGS. 5A and 5B, the probe 20 is fitted into the probe connection portion 34 and the probe clamp portion 37 of the drive unit 13 by the user, and is connected and fixed to the drive unit 13. Then, the probe 20 is inserted to a target site in the blood vessel. Then, the diagnosis support system 10 pulls back the ultrasound transducer 25 while rotating the ultrasound transducer 25 around the central axis of the probe 20, and starts capturing the IVUS image.

In S11 of FIG. 5A, the control unit 41 generates frame data of an IVUS image. In the present embodiment, an example in which the diagnosis support device 11 generates and acquires the frame data before the polar coordinate conversion and performs the processing of each step of FIGS. 5A and 5B will be described. However, the same processing may be performed on the frame data after the polar coordinate conversion. Hereinafter, a frame image to be subjected to the processing of S12 to S30 is referred to as a "target frame".

Next, the control unit 41 performs processing of S12 to S17 on each pixel included in the target frame, and determines whether or not the pixel is included in a specific region such as a blood flow region. Hereinafter, the pixel to be processed is referred to as an "attentional pixel".

In S12, the control unit 41 determines whether the luminance of the attentional pixel is larger than a predetermined threshold value $T_1$. If it is large (YES in S12), the processing proceeds to S16, and if not large (NO in S12), the processing proceeds to S13. The threshold value $T_1$ can be determined according to, for example, the type of catheter, the frequency mode, or the like.

In S13, the control unit 41 extracts a region of interest (ROI) from the frame data around the attentional pixel. Here, an example in which the region of interest is 15×15×15 pixels in two spatial directions and one time direction will be described, but the shape and size of the region of interest are not limited to this, and can be appropriately set according to the resolution of the image or the like. In addition, the shape and size of the region of interest may be different depending on the type of the spatiotemporal feature (spatiotemporal feature amount) calculated in S14.

In S14, the control unit 41 calculates (computes) two spatiotemporal features a and b based on the luminance value of the pixel included in the region of interest. In the present embodiment, an example will be described in which a correlation coefficient R between frame images is used as such a spatiotemporal feature a, and a ratio q between a luminance average of neighboring pixels and a luminance dispersion of neighboring pixels is used as the spatiotemporal feature b.

Figure 6A:
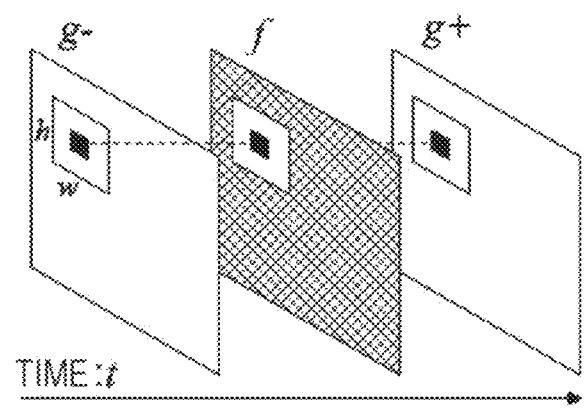
FIG. 6A is a diagram illustrating an example of spatiotemporal features in an IVUS image.

FIG. 6A illustrates an example of calculating a correlation coefficient between frame images. In FIG. 6A, f represents a target frame acquired at time t, $g^-$ represents a previous frame image acquired at time (t−1), and $g^+$ represents a next frame image acquired at time (t+1). The value R ($d_x$, $d_y$) of the correlation coefficient in the attentional pixel is calculated by the following formula.

Mathematical formula 1

$$R(d_x, d_y) = \frac{\sum_{x=0}^{w-1} \sum_{y=0}^{h-1} [f(d_x + x, d_y + y) - \bar{f}][g(d_x + x, d_y + y) - \bar{g}]}{\sqrt{\sum_{x=0}^{w-1} \sum_{y=0}^{h-1} [f(d_x + x, d_y + y) - \bar{f}]^2} \sqrt{\sum_{x=0}^{w-1} \sum_{y=0}^{h-1} [g(d_x + x, d_y + y) - \bar{g}]^2}}$$

provided that:

$\bar{f}$: Average value of image (t), and $\bar{g}$: Average value of image (t±1).     Mathematical formula 2

In addition, ($d_x$, $d_y$) is the coordinates of the attentional pixel in the target frame. In the example of FIG. 6A, the correlation coefficient between adjacent frame images (target frame image f and adjacent frame images $g^+$ or $g^-$) is calculated with the attentional pixel as the center and a height h and a width w as the window sizes. In the present embodiment, the window size is 15×15 similarly to the size of the region of interest in the spatial direction, but is not limited to this. The window size can be, for example, a distance between two speckle noise peaks. This distance can be calculated from the duration of the pulse waveform calculated as the full width at half maximum of the autocorrelation coefficient including noise.

In general, since various blood cells exist in the blood flow region, it is known that uniformity of an ultrasound image is relatively low and a correlation coefficient between frame images is relatively small for the blood flow region.

On the other hand, since a stent, a calcified portion, or the like are uniformly formed in the inside of the stent and calcified portion, it is known that uniformity of an ultrasound image is relatively high and a correlation coefficient between frame images is relatively large for a stent, a calcified portion and the like It is known that the correlation coefficient between frame images is intermediate between tissue and fiber plaque portions.

Figure 6B:
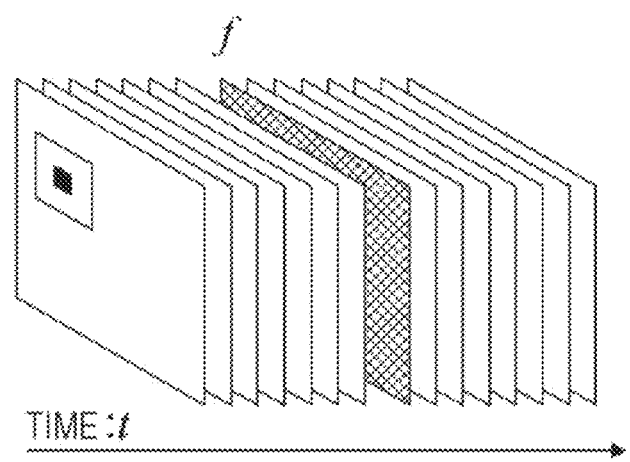
FIG. 6B is a diagram illustrating an example of spatiotemporal features in an IVUS image.

FIG. 6B illustrates an example of calculating the ratio between a luminance average of neighboring pixels and a luminance dispersion of neighboring pixels. A ratio $q_0$ (t) between a luminance average of neighboring pixels and a luminance dispersion of neighboring pixels in the attentional pixel is calculated by the following formula $$q_0(t) = \frac{\sqrt{\text{var}[z(t)]}}{\overline{z(t)}}$$ Mathematical formula 3 provided that:

var[z(t)]: Luminance dispersion of ROI, and $\overline{z(t)}$:
Luminance average of ROI.  Mathematical formula 4

As shown in Mathematical formula 3, $q_0$ (t) is calculated by dividing the square root of the luminance dispersion of the region of interest (ROI) by the luminance average of the region of interest. It is known that the ratio between the luminance average and the luminance dispersion is relatively low in the blood flow region, relatively high in the regions of the tissue and the fiber plaque, and intermediate between the stent and the calcified portion.

Figure 7:
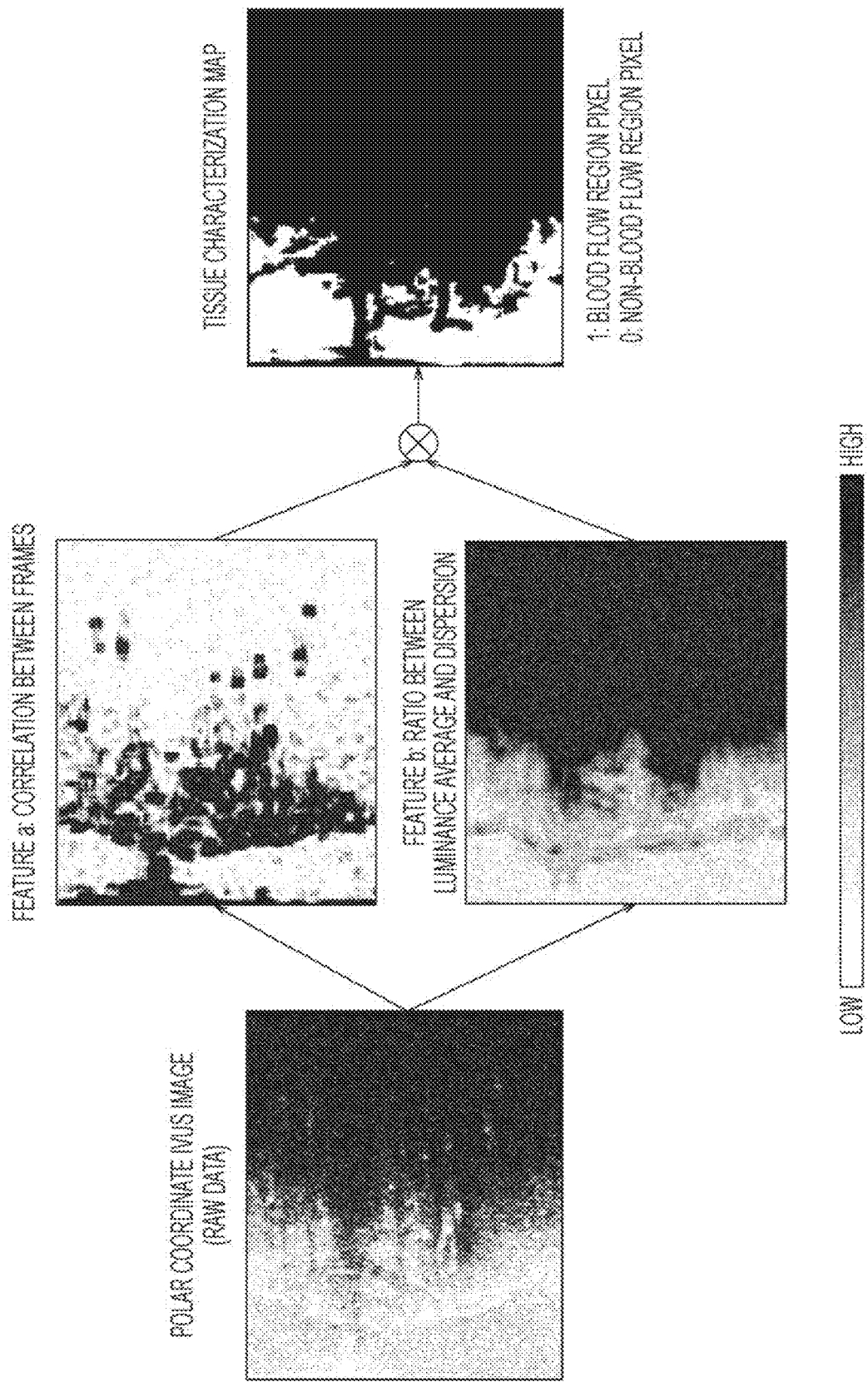
FIG. 7 is a diagram illustrating an example of extracting a blood flow region from an IVUS image based on a plurality of spatiotemporal features.

As described above, it is known that the value of the spatiotemporal feature calculated in S14 varies depending on the type of the region where the attentional pixel exists. Specifically, it is known that both the spatiotemporal feature a (correlation coefficient between frame images) and the spatiotemporal feature b (ratio between luminance average of neighboring pixels and luminance dispersion of neighboring pixels) are relatively small in the blood flow region. Therefore, in the present embodiment, the control unit 41 determines a region where both of the spatiotemporal features a and b fall below a predetermined threshold value as a blood flow region. Specifically, as illustrated in FIG. 7, the control unit 41 generates maps of the spatiotemporal features a and b from the IVUS image before the polar coordinate conversion, determines a range in which both values of the spatiotemporal features a and b are small as blood flow region pixels, and determines the other ranges as non-blood flow region pixels. Then, the control unit 41 generates a tissue characterization map M ($r_i$, $\theta_j$) including the blood flow region (pixel value=1) and other regions (pixel value=0) in FIG. 7. Here, $r_i$ is a distance from the ultrasound transducer 25, and $\theta_j$ is a rotation angle from a reference angle.

In S15, the control unit 41 determines whether the spatiotemporal feature a (correlation coefficient between frame images) falls below a predetermined threshold value $T_2$ and whether the spatiotemporal feature b (ratio between the luminance average of the neighboring pixels and the luminance dispersion of the neighboring pixels) falls below a predetermined threshold value $T_3$. In a case where the spatiotemporal feature a is not below the threshold value $T_2$ or if the spatiotemporal feature b does not fall below the threshold value $T_3$ (NO in S15), the processing proceeds to S16. In a case where the spatiotemporal feature a falls below the threshold value $T_2$ and the spatiotemporal feature b falls below the threshold value $T_3$ (YES in S15), the processing proceeds to S17.

In S16, the control unit 41 determines that the attentional pixel is not a blood flow region, sets M ($r_i$, $\theta_j$)=0, and proceeds to S18. In S17, the control unit 41 determines that the attentional pixel is a blood flow region, sets M ($r_i$, $\theta_j$)=1, and proceeds to S18.

In S18, the control unit 41 determines whether or not the processing of S12 to S17 has been performed on all the pixels of the target frame. If not (NO in S18), the process returns to S12, and the processing in S12 to S17 is executed with the unprocessed pixel as the attentional pixel. If yes (YES in S18), the processing proceeds to S19 in FIG. 5B.

In S19 to S23, the control unit 41 performs processing of excluding a region that is determined to be a blood flow region in the tissue characterization map (M ($r_i$, $\theta_j$)=1) but has an extremely small size from the blood flow region (that is, M ($r_i$, $\theta_j$)=0).

In S19, the control unit 41 counts the number of pixels included in one continuous blood flow region in the tissue characterization map. In S20, the control unit 41 determines whether or not a counted value N exceeds a predetermined threshold value $T_4$. If the counted value N does not exceed the threshold value $T_4$ (NO in S20), the processing proceeds to S21, and if the counted value N exceeds the threshold value $T_4$ (YES in S20), the processing proceeds to S22.

In S21, the control unit 41 sets the value M ($r_i$, $\theta_j$) of the tissue characterization map for the attentional pixel to 0, and proceeds to S23. In S22, the control unit 41 sets the value M ($r_i$, $\theta_j$) of the tissue characterization map for the attentional pixel to 1, and proceeds to S23.

In S23, the control unit 41 determines whether or not the processing in S19 to S22 has been performed on all the pixels of the target frame. If yes (YES in S23), the processing proceeds to S24. If not (NO in S23), the process returns to S19, and the process in and after S19 is performed on the unprocessed pixel.

In S24, the control unit 41 scans each line in the R direction, and sets the R coordinate n having the maximum luminance value among the non-blood flow region pixels as the boundary of the blood flow region. Next, in S25, the control unit 41 sets the entire outside of the boundary of the blood flow region as a non-blood flow region. That is, in a case where $r_i \geq r_i$, the control unit 41 performs processing of setting the tissue characterization map M ($r_i$, $\theta_j$)=0.

Then, in S26, the control unit 41 determines whether or not the processing of S24 and S25 has been performed for all the lines. If yes (YES in S26), the processing proceeds to S27. If not (NO in S26), the process returns to S24, and the similar processing is performed on the unprocessed line.

Figure 8:
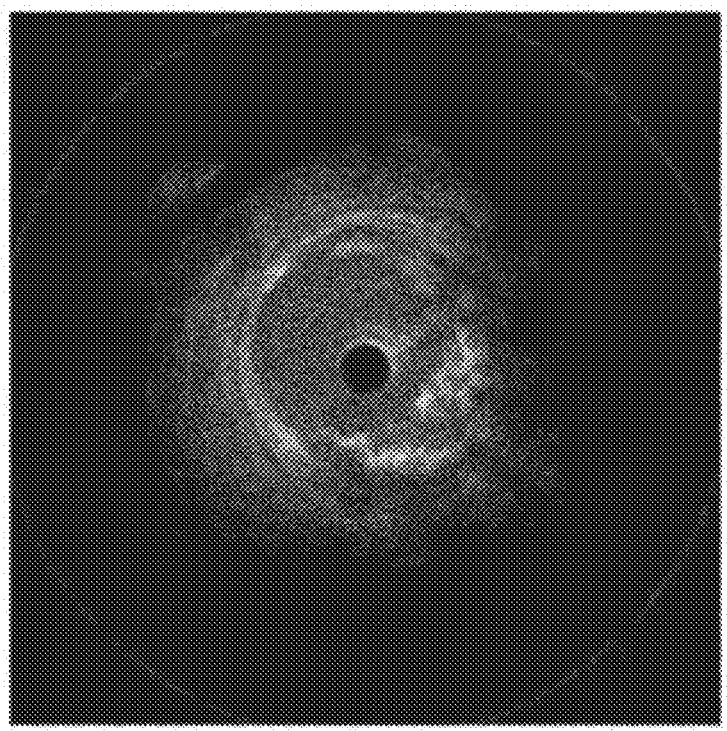
FIG. 8 is a diagram illustrating an example of applying post-processing to an IVUS image.
Figure 8:
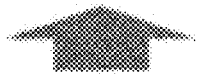
Figure 8:
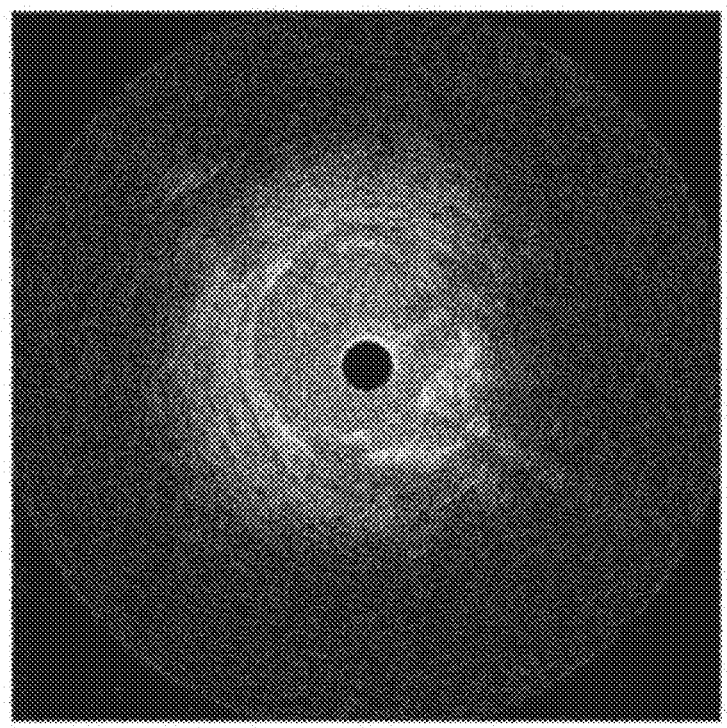

In S27 to S29, the control unit 41 performs processing of suppressing the luminance value by applying a minimum value filter for each pixel determined to be the blood flow region (M ($r_i$, $\theta_j$)=1) in the tissue characterization map. FIG. 8 illustrates an example of images before and after suppressing the luminance value in the blood flow region. By performing post-processing such as luminance value suppression, the user can rather easily visually distinguish the blood flow region and the other regions.

In S27, the control unit 41 determines whether or not a blood flow region (M ($r_i$, $\theta_j$)=1) is set in the tissue characterization map by the processing up to S26. In a case where the blood flow area is set (YES in S27), the processing proceeds to S28, and in a case where the blood flow region is not set (NO in S27), the processing proceeds to S29. In S28, the control unit 41 performs processing of suppressing the luminance value by applying the minimum value filter, and proceeds to S29.

In S29, the control unit 41 determines whether or not the processing of S27 and S28 has been performed on all the pixels of the target frame. If yes (YES in S29), the processing proceeds to S30, and if not (NO in S29), the process returns to S27.

In S30, the control unit 41 outputs a blood cell noise-reduced image $I_{out(t)}$ subjected to the processing in S12 to S29. Then, in S31, the control unit 41 determines whether or not there is a next frame image. In a case where there is an image (YES in S31), the processing returns to S12, and in a case where there is no image (NO in S31), the processing ends.

As described above, in the present embodiment, the specific region such as the blood flow region is extracted from the IVUS image based on the ratio between the average of the luminance in the region of interest included in the IVUS image and the dispersion of the luminance in the region of interest. Therefore, it is possible to identify an observation target with relatively higher accuracy from a result of observing a cross section of a biological tissue by ultrasound.

In the present embodiment, the example in which the biological tissue to be observed is a blood vessel has been described, but the biological tissue may be an organ such as a heart or other biological tissue. In addition, in the present embodiment, the example in which the region to be distinguished as the specific region is the blood flow region of the observation target has been described, but the present disclosure is not limited to this, and the region may be a stent, a guide wire, a blood vessel wall, a calcified lesion, a plaque, or another reflector.

In addition, in the present embodiment, the control unit 41 acquires a plurality of frame images as IVUS images. Then, the control unit 41 extracts the specific region based on the ratio between the average of the luminance in the region of interest and the dispersion of the luminance in the region of interest as well as the feature amount of at least one of the feature amount in the time direction and the feature amount in the spatial direction of the plurality of frame images. Specifically, the control unit 41 extracts the specific region based on the correlation of the luminance between the frame images in addition to the ratio to the dispersion of the luminance. Therefore, by using not only a single feature amount but also a plurality of feature amounts, it is possible to extract a specific region with relatively higher accuracy.

In the present embodiment, as the spatiotemporal feature used to extract the specific region, the ratio between the average of the luminance in the region of interest and the dispersion of the luminance in the region of interest, and the correlation coefficient between the frame images are used. However, the present disclosure is not limited to this. The control unit 41 may use, for example, a frequency feature (a power spectrum ratio between a low frequency component and a high frequency component, or the like), a texture feature (a local binary pattern (an LBP) feature amount, or the like), or the like. Furthermore, in addition to these, the control unit 41 may use general image feature amounts such as image statistics (normal distribution, Rayleigh distribution), histogram skewness, kurtosis, and second order moment in combination.

As described with reference to FIG. 7, in the present embodiment, the control unit 41 extracts the first region from the plurality of frame images based on the ratio between the average of the luminance in the first region of interest included in the plurality of frame images and the dispersion of the luminance in the first region of interest. Furthermore, the control unit 41 extracts the second region from the plurality of frame images based on at least one feature amount in the second region of interest included in the plurality of frame images. Then, the control unit 41 determines a region commonly included in the first region and the second region as a specific region such as a blood flow region. Therefore, it is possible to extract the specific region with relatively higher accuracy using a plurality of feature amounts.

In the present embodiment, whether or not the attentional pixel is included in a specific region such as a blood flow region or its candidate is determined based on whether or not a spatiotemporal feature such as a ratio to dispersion of luminance in the region of interest and correlation of luminance between frame images is less than a predetermined threshold value (first value, second value). Therefore, according to the present embodiment, the specific region can be rather efficiently extracted.

In the present embodiment, in S27 to S29, the contrast between the region included in the specific region and the region not included in the specific region is enhanced in at least one frame image. Specifically, the luminance of the region included in the specific region is suppressed in at least one frame image. Therefore, according to the present embodiment, by displaying the image subjected to such processing on the display 16, the user can rather easily distinguish and visually recognize the specific region such as the blood flow region.

The method of distinguishing the region included in the specific region from the region not included in the specific region and displaying at least one frame image on the display unit is not limited to the contrast adjustment. For example, the control unit 41 may cause the display unit to display at least one frame image by making display colors different between a region included in the specific region and a region not included in the specific region. Alternatively, the control unit 41 may display at least one frame image on the display unit by making the transparency of the region included in the specific region higher than the transparency of the region not included in the specific region. As described above, the region included in the specific region and the region not included in the specific region are distinguished and displayed, in a manner that the user can rather easily distinguish the specific region and the other regions by visual recognition.

Modification

In the configuration described with reference to FIGS. 5A and 5B, one specific region called the blood flow region is extracted based on the ratio between the average of the luminance in the region of interest and the dispersion of the luminance in the region of interest for the attentional pixel included in the IVUS image. However, the specific region to be extracted is not limited to one type, and a plurality of types of specific regions may be extracted (see FIG. 9).

Figure 9:
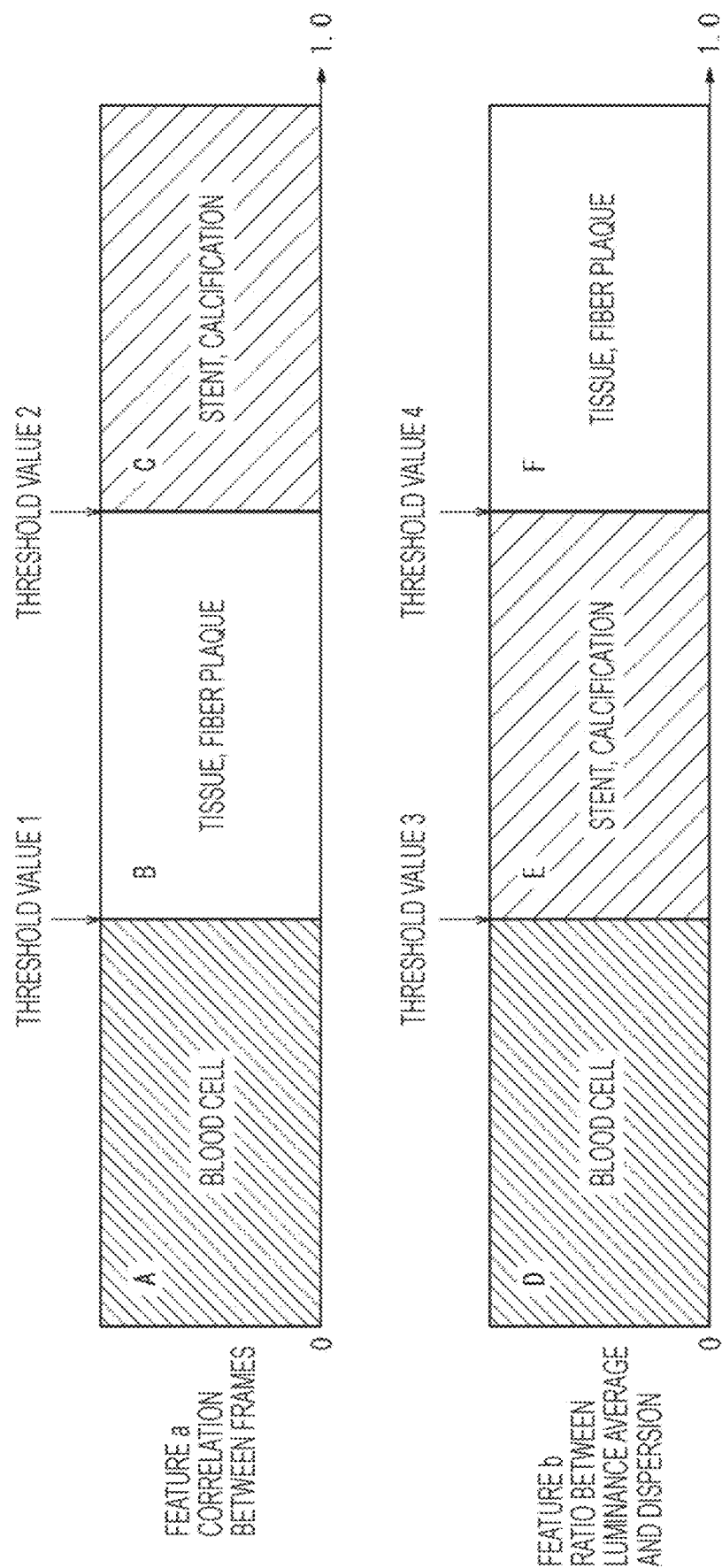
FIG. 9 is a diagram illustrating an example of extracting a plurality of regions from an IVUS image based on a plurality of spatiotemporal features.

As described above, it is known that the correlation coefficient between frame images is generally small in the blood flow region, the correlation coefficient between frame images is relatively large in the stent and the calcified portion, and the correlation coefficient between frame images is intermediate between these in the tissue and the fiber plaque. Therefore, the control unit 41 may extract a plurality of types of specific regions from the frame image based on which of a plurality of predetermined numerical ranges the ratio between the average of the luminance in the region of interest and the dispersion of the luminance in the region of interest for the attentional pixel included in the frame image belongs to. In the example of FIG. 9, the control unit 41 compares the magnitudes of the ratio between the average of the luminance and the dispersion of the luminance in the region of interest and the threshold value 3 and the threshold value 4 for each attentional pixel, and determines which of the numerical ranges D, E, and F the attentional pixel belongs to. Then, the control unit 41 may extract specific regions of blood cells, stent/calcification, and tissue/fiber plaque based on such a determination result for each attentional pixel.

In addition, as described above, it is known that the ratio between the luminance average and the luminance dispersion is relatively low in the blood flow region, relatively high in the regions of the tissue and the fiber plaque, and intermediate between the stent and the calcified portion. Therefore, the control unit 41 may extract a plurality of specific regions by using not only the ratio between the average of the luminance in the region of interest and the dispersion of the luminance in the region of interest for the attentional pixel described above but also such properties for a plurality of spatiotemporal features in combination.

That is, the control unit 41 determines which of a plurality of predetermined numerical ranges (first numerical ranges) the ratio between the average of the luminance in the first region of interest and the dispersion of the luminance in the first region of interest for the first attentional pixel included in the plurality of frame images belongs to. Furthermore, the control unit 41 determines which of a plurality of predetermined numerical ranges (second numerical ranges) the at least one feature amount in the second region of interest for the second attentional pixel included in the plurality of frame images belongs to. Then, the control unit 41 may extract a plurality of specific regions from a plurality of types of frame images based on these determination results. As a result, a plurality of specific regions can be extracted with relatively high accuracy based on a plurality of spatiotemporal features. In the example of FIG. 9, the control unit 41 compares the magnitudes of the ratio between the average of the luminance and the dispersion of the luminance in the region of interest and the threshold value 3 and the threshold value 4 for each attentional pixel, and determines which of the numerical ranges D, E, and F the attentional pixel belongs to. Furthermore, the control unit 41 compares the magnitudes of the correlation coefficient between the frames in the region of interest with the threshold value 1 and the threshold value 2 for each attentional pixel, and determines which of the numerical ranges A, B, and C the attentional pixel belongs to. Then, the control unit 41 may extract specific regions of blood cells, stent/calcification, and tissue/fiber plaque based on these determination results.

As the spatiotemporal feature amount, a correlation coefficient between frame images, a frequency feature, a texture feature, or the like may be used, and in addition to these, general feature amounts of an image such as image statistics, histogram skewness, kurtosis, and second order moment in combination.

The present disclosure is not limited to the above-described embodiments. For example, a plurality of blocks described in the block diagram may be integrated, or one block may be divided. Instead of executing the plurality of steps described in the flowcharts in chronological order according to the description, the steps may be executed in parallel or in a different order, depending on the processing capability of the device executing the steps or as needed. In addition, modifications can be made without departing from the gist of the present disclosure.

The detailed description above describes embodiments of an information processing device, an information processing system, an information processing method, and a computer program. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. An information processing device comprising:
a control unit configured to:
acquire a plurality of frame images generated by using line data indicating intensity of a reflection wave with respect to an ultrasound radially transmitted from an ultrasound transducer moving inside a biological tissue;
extract a first region from the plurality of frame images based on a ratio between an average of luminance in a first region of interest included in the plurality of frame images and a dispersion of luminance in the first region of interest;
extract a second region from the plurality of frame images based on at least one feature amount in a second region of interest included in the plurality of frame images; and
determine a region commonly included in the first region and the second region as a specific region.

2. The information processing device according to claim 1, wherein the control unit is configured to:
extract the specific region based on at least one of feature amounts of the plurality of frame images in a time direction and a feature amount in another spatial direction.

3. The information processing device according to claim 1, wherein in a case where a ratio between an average of luminance in a first region of interest and a dispersion of luminance in a first region of interest for a first attentional pixel included in the plurality of frame images falls below a predetermined first value, the control unit is configured to determine that the first attentional pixel is included in the first region.

4. The information processing device according to claim 2, wherein the control unit is configured to calculate, as a feature amount in the time direction, a correlation of luminance between different frame images in the second region of interest for a second attentional pixel included in the plurality of frame images.

5. The information processing device according to claim 4, wherein the control unit is configured to determine that the second attentional pixel is included in the second region in a case where the feature amount in the time direction falls below a predetermined second value.

6. The information processing device according to claim 1, wherein the control unit is configured to determine the specific region as a blood flow region.

7. The information processing device according to claim 1, wherein the control unit is configured to enhance contrast between a region included in the specific region and a region not included in the specific region in the plurality of frame images.

8. The information processing device according to claim 7, wherein the control unit is configured to suppress luminance of the region included in the specific region in the at least one frame image.

9. The information processing device according to claim 1, wherein the control unit is configured to display at least one frame image of the plurality of frame images on a display unit by distinguishing the region included in the specific region from the region not included in the specific region.

10. The information processing device according to claim 9, wherein the control unit is configured to display the at least one frame image on the display unit by making display colors different between the region included in the specific region and the region not included in the specific region.

11. The information processing device according to claim 9, wherein the control unit is configured to:
display the at least one frame image on the display unit by making transparency of the region included in the specific region higher than transparency of the region not included in the specific region.

12. The information processing device according to claim 1, wherein the control unit is configured to:
extract a plurality of types of the specific regions from at least one frame image of the plurality of frame images based on which of a plurality of predetermined numerical ranges a ratio between an average of luminance in the first region of interest and the dispersion of luminance in the first region of interest for a first attentional pixel included in the at least one frame image.

13. The information processing device according to claim 1, wherein the control unit is configured to:
extract a plurality of types of the specific regions from the plurality of frame images based on which of a plurality of predetermined first numerical ranges a ratio between an average of luminance in the first region of interest and the dispersion of luminance in the first region of interest for a first attentional pixel included in the plurality of frame images, and which of a plurality of predetermined second numerical ranges the at least one feature amount in the second region of interest for a second attentional pixel included in the plurality of frame images.

14. An information processing system comprising:
the information processing device according to claim 1; and
a probe including the ultrasound transducer.

15. An information processing method, comprising:
acquiring, by a control unit of an information processing device, a plurality of frame images generated by using line data indicating intensity of a reflection wave with respect to an ultrasound radially transmitted from an ultrasound transducer moving inside a biological tissue;
extracting, by the control unit of the information processing device, a first region from the plurality of frame images based on a ratio between an average of luminance in a first region of interest included in the plurality of frame images and a dispersion of luminance in the first region of interest;
extracting, by the control unit of the information processing device, a second region from the plurality of frame images based on the at least one feature amount in a second region of interest included in the plurality of frame images; and
determining, by the control unit of the information processing device, a region commonly included in the first region and the second region as a specific region.

16. The information processing method according to claim 15, further comprising:
extracting, by the control unit of the information processing device, the specific region based on at least one of feature amounts of the plurality of frame images in a time direction and a feature amount in another spatial direction.

17. The information processing method according to claim 15, wherein in a case where a ratio between an average of luminance in a first region of interest and a dispersion of luminance in a first region of interest for a first attentional pixel included in the plurality of frame images falls below a predetermined first value, further comprising:
determining, by the control unit of the information processing device, that the first attentional pixel is included in the first region.

18. A non-transitory computer-readable medium storing a computer program executed by a computer processor to execute a process comprising:
acquiring a plurality of frame images generated by using line data indicating intensity of a reflection wave with respect to an ultrasound radially transmitted from an ultrasound transducer moving inside a biological tissue;
extracting a first region from the plurality of frame images based on a ratio between an average of luminance in a first region of interest included in the plurality of frame images and a dispersion of luminance in the first region of interest;
extracting a second region from the plurality of frame images based on at least one feature amount in a second region of interest included in the plurality of frame images; and
determining a region commonly included in the first region and the second region as a specific region.

* * * * *